US006423038B1

(12) United States Patent
Vancaillie

(10) Patent No.: US 6,423,038 B1
(45) Date of Patent: *Jul. 23, 2002

(54) TOPICAL INTRA-UTERINE ANESTHESIA DEVICE AND METHOD

(76) Inventor: Thierry G. Vancaillie, 60 Sugarloaf Crescent, Castlecrag N.S.W. 2068 (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/175,233

(22) Filed: Oct. 20, 1998

(51) Int. Cl.$^7$ ............................................... A61M 31/00
(52) U.S. Cl. ..................................... 604/279; 604/288
(58) Field of Search ................................ 604/329, 213, 604/239, 240, 514, 515, 911, 285, 288, 279, 278

(56) References Cited

U.S. PATENT DOCUMENTS

| 3,626,928 A | | 12/1971 | Van Rensselaer et al. |
| 4,071,027 A | * | 1/1978 | Meador ...................... 604/515 |
| 4,430,076 A | * | 2/1984 | Harris ..................... 604/103.03 |
| 4,432,758 A | * | 2/1984 | Finegold ................. 604/288 X |
| 5,338,297 A | | 8/1994 | Kocur et al. |
| 5,569,241 A | | 10/1996 | Edwards |

FOREIGN PATENT DOCUMENTS

| BE | 633 372 | 10/1963 |
| DE | 35 16830 A1 | 11/1986 |

OTHER PUBLICATIONS

Hasson, H. M., "Topical Uterine Anesthesia: A preliminary Report" Int. J. Gynaecol. Obster. vol. 15, pp. 238–240.*
Hasson, H.M., "Topical Uterine Anesthesia: A Preliminary Report" Int. J. Gynaecol. Obstet. vol. 15, pp. 238–240 (1977).
Hollingsworth, B., "Pain control during insertion of an intrauterine device" The British Journal of Family Planning, vol. 21, No. 3.
Rabin et al., "Instruments and Methods", Obstetrics & Gynecology, vol. 73, No. 6, Jun. 1989, pp. 1040–1044.
Schellen, "Intrauterine Anasthesia: A New Approach" Int. J. Fertil., vol. 28, No. 1, 1983, pp. 57–58.

* cited by examiner

Primary Examiner—Anhtuan T. Nguyen
(74) Attorney, Agent, or Firm—Fish & Richardson P.C.

(57) ABSTRACT

A topical anesthesia device comprising an injection device having a plunger at one end and an injection opening at the other end. A hollow tube is attached to the injection opening of the injection device. The tube is curved towards the distal tip, having multiple orifices, one orifice being at the distal tip of the tube and remaining orifices being in the sidewalls of the tube. The tube is inserted through the vagina until the resistance of the fundus is perceived and the injection device is operated to permit the anesthetic to exit the orifices on the sidewall of the tube in the region of the tubal ostium and/or the comua of the uterus such that the anesthetic displaces intrauterine debris to reach the mucosal surface of the uterus. The topical anesthesia device provides a significant improvement over the efficiency of the conventional intra-uterine anesthesia devices.

16 Claims, 3 Drawing Sheets

TOPICAL INTRA-UTERINE ANESTHESIA DEVICE AND METHOD

TECHNICAL FIELD

The invention relates to methods and apparatus for topical intra-uterine anesthesia.

BACKGROUND

Physicians commonly use topical anesthesia to reduce pain associated with uterine manipulations during gynecological procedures. Conventional anesthesia devices and methods suffer from several disadvantages. An example of a conventional, commercially available device for topical intra-uterine anesthesia is depicted in FIG. 1. Such devices 10 typically include a frontal, soft perforated tube 12 attached to a pliable acorn 14, which is connected to a syringe 16. The method for using such devices involves inserting the tube 12 into the cervical canal (normally collapsed) until the pliable acorn 14 abuts the external cervical os. The syringe 16 is used to introduce an anesthetic (e.g., Lidocaine® or Marcaine®) through the perforated tube 12 to anesthetize the immediately surrounding tissue. The pliable acorn 14 blocks the cavity of the cervix and prevents the back-flow of the anesthetic through the vagina. After the pliable acorn 14 is withdrawn, a small portion of the anesthetic may leak out; the remaining anesthetic is predominantly absorbed by the cervical mucous membrane.

Such conventional anesthesia devices suffer from several disadvantages. For example, these devices do not include a frontal portion that is long enough to reach the tubal ostium. Consequently, conventional anesthesia devices permit application of anesthetic to the cervix, which is of limited clinical use, rather than the target area, which is mainly the tubal ostium. The straight angle of the conventional frontal tube makes it difficult to direct the anesthetic towards the tubal ostium. Conventional anesthesia devices also inject the anesthetic into the cavity through the cervix, which displaces intrauterine debris such as mucus and menstrual blood toward the fundus and uterine cornua. This prevents the anesthetic from reaching its target, i.e., the mucosal surface of the uterine cavity and cornua.

Furthermore, such conventional anesthesia devices are typically designed with rigid frontal tubes made out of rigid plastic or metal material. Such construction, however, makes it difficult to direct the anesthetic to desired regions of the patient's uterus. Further, any effort to direct the frontal tube in a particular direction is likely to result in increased discomfort to the patient.

Another conventional mechanism for anesthetic application to the cervix involves the use of a procto-swab or a cotton tipped applicator coated with anesthetic gel (e.g., benzocaine 20% gel, 2% lignocaine gel, or Instillagel®[2% lignocaine+0.25% chlorhexidine]). The swabs are inserted through the vagina into the cervix. This process also has several disadvantages. For example, the gel is hydrophobic and is rendered ineffective to some extent as it passes through the mucus present in the vagina and the cervix. Another disadvantage is that the gel typically rubs off on the vaginal wall, reducing the amount of gel applied to the cervix and also resulting in application of anesthetic to an undesired region of the patient's genital tract. The swab is also typically made of rigid material to increase the ease of the insertion. However, the rigidity of the swab makes it difficult to direct the gel to the desired region. Another significant disadvantage of using a swab is that it increases the likelihood of passage of pathogens from the lower to the upper genital tract.

SUMMARY

The invention relates to a topical intra-uterine anesthesia device (IUAD) which is intended to apply anesthetic to the mucosal surface of the uterine cavity and the tubal ostium. In the preferred embodiment of the invention, an intrauterine applicator is combined with an injection device, such as a syringe. For purposes of this description, this invention is described in the context of using a syringe. The applicator preferably includes a thin, hollow, slightly inclined, frontal tube having an orifice at the distal tip of the tube and one or more orifices on the sides of the tube near the distal tip. In use, the applicator is inserted through the vagina into the cervical cavity, and is gently pushed until the tip reaches the fundus. The slight inclination of the frontal tube allows the anesthetic to be directed towards either one or the other tubal ostium and the cornua of the uterus. If the IUAD is used without an acorn for preventing the back-flow of the anesthetic through the vagina, observation of anesthetic back-flow through the vagina may provide evidence of the sufficiency of volume used of the anesthetic.

The orifices at the distal tip of the hollow tube perforate the wall of the tube at a forward oblique angle. This provides a preferential path for the anesthetic. This preferential path is important because the anesthetic will be directed toward the fundus or ostium thereby displacing intra-uterine debris toward the lateral walls of the uterine cavity. Once the anesthetic material fills the space near the fundus and tubal ostium, it will continue to displace intra-uterine debris toward the cervix and out into the vagina. Displacement of the intrauterine debris away from the mucosal surface allows the anesthetic material to establish direct contact with the mucosal surface. Direct contact between the anesthetic and mucosal surface is necessary for the anesthetic to take effect.

The frontal tube is preferably made of a semi-flexible plastic or other material appropriate for the particular application. As described below, the frontal tube may have more than the orifice at the distal tip of the tube. In particular, the frontal tube may include orifices on the sidewalls. The orifices at the distal tip of the hollow tube are positioned, shaped, and aligned such that the anesthetic is directed toward the tubal ostium and the fundus, regardless of whether one or more of the orifices is obstructed by (1) the fundus or other uterine wall; or (2) anatomic variations of an individual's uterus.

Embodiments of the invention provide significant advantages in that the physician can apply anesthetic to the mucosal surface of the tubal ostium even without accurately locating the same. Consequently, the efficiency of applying topical anesthetic to the mucosal surface of the uterine cavity and uterine cornua is significantly increased.

DETAILED DESCRIPTION

The following detailed description is of the best presently contemplated mode of carrying out the invention. This description is not to be taken in a limiting sense, but is merely made for the purpose of illustrating the general principles of embodiments of the invention. The scope of the invention is defined only by the appended claims.

While various embodiments of the invention may also be suitable for other surgical and diagnostic procedures, the preferred embodiment is directed to using it as an intra-uterine anesthesia apparatus and method.

Figure 1:
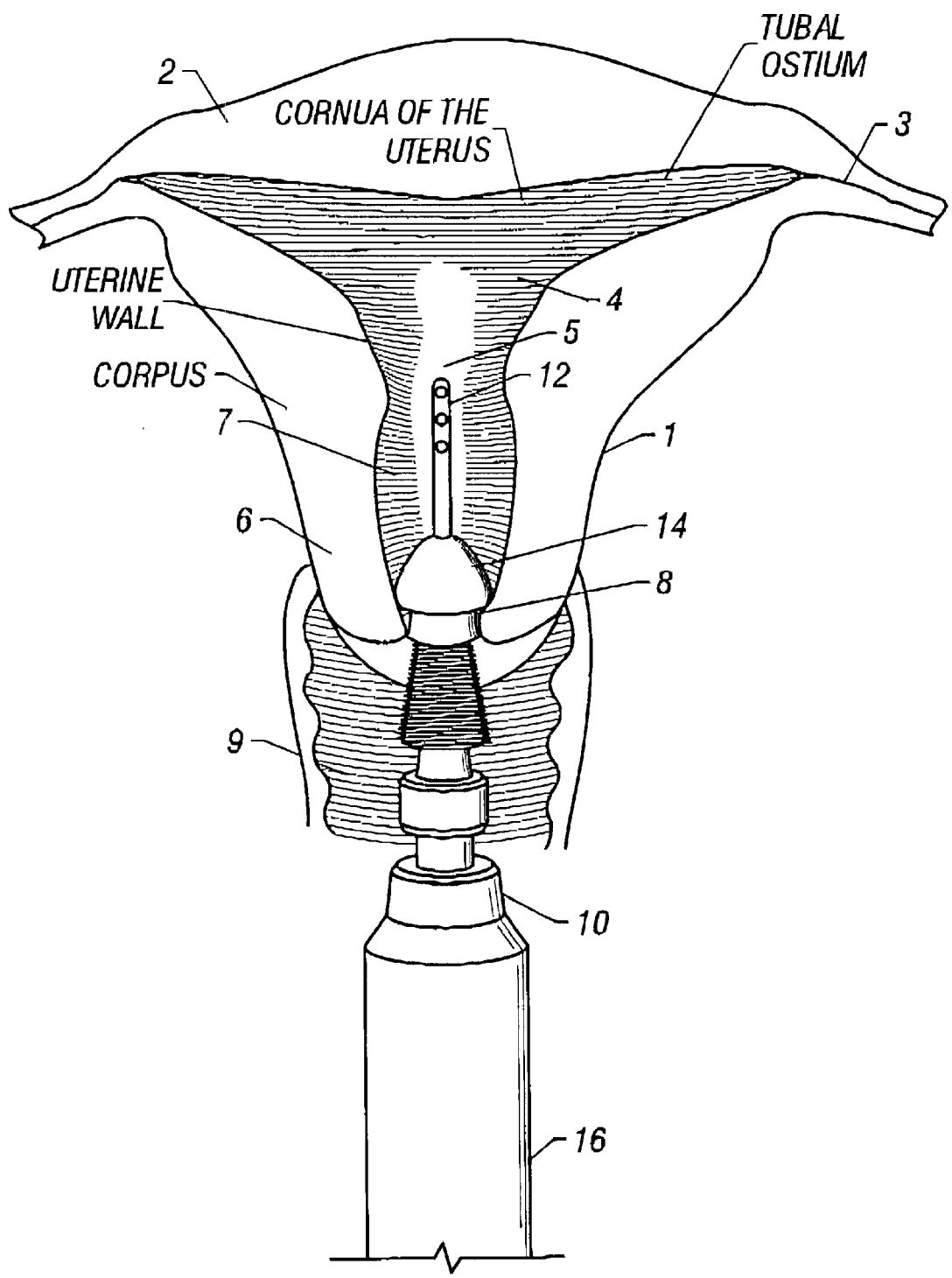
FIG. 1 is a frontal schematic view of a portion of a prior art topical intra-uterine anesthesia device depicting its placement in a uterus.

FIG. 1 includes a depiction of a uterus. The uterus, hollow, thick-walled and muscular 1, is normally situated in the lesser pelvis between the urinary bladder and the rectum. The fundus 2 forms the upper part of the uterus, which opens through the uterine cornua into the uterine tubes 3, one on each side ("tubal ostium"); below, the uterus opens into the corpus of the body 4. The corpus 4 narrows to a constriction corresponding to the narrowing of the cavity of the body at the internal os 5. The part below the corpus of the body is the cervix 6, which includes the cavity of the cervix 7. The cavity of the cervix 7 is more cylindrical than the corpus, and is widest at its mid-level. At the bottom, the cervix narrows to the external os 8, where it opens to the vaginal region 9. The invention is directed to an apparatus and method for applying anesthetic to the tubal ostium region.

Figure 2B:
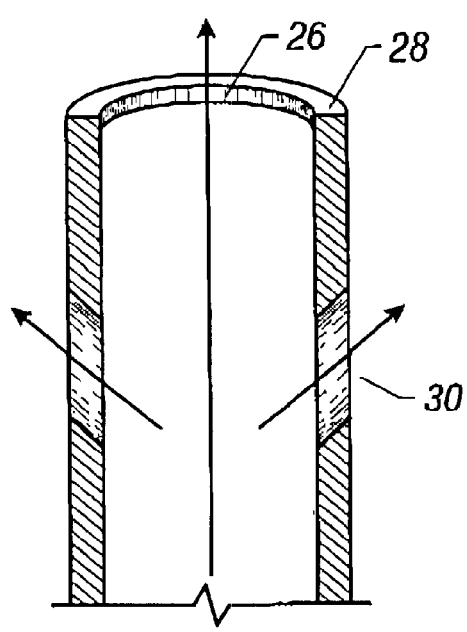
FIG. 2(b) is a detailed drawing of the distal tip of the frontal tube of the topical intra-uterine anesthesia device.
Figure 2A:
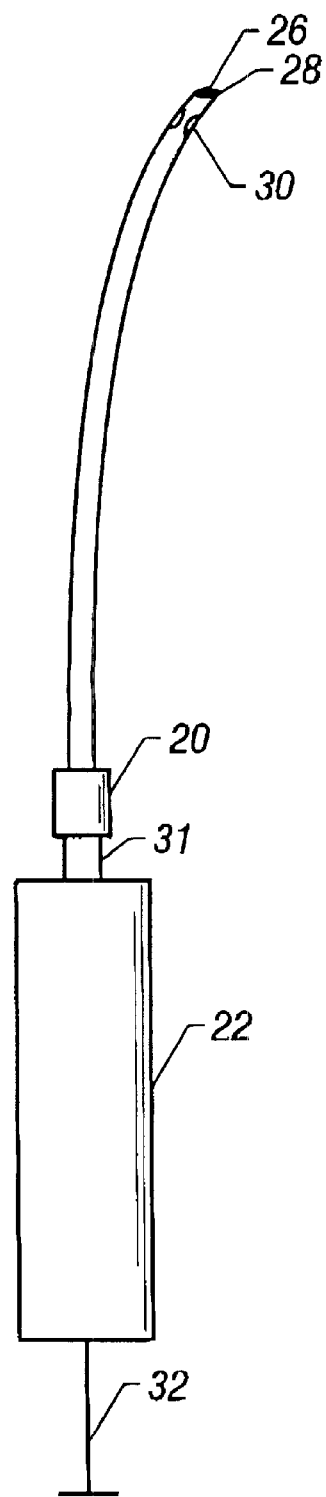
FIG. 2(a) is a side view of a topical intra-uterine anesthesia device according to one embodiment of the present invention.

FIG. 2(a) is a frontal view of a topical intra-uterine anesthesia device according to an embodiment of the invention. As illustrated in FIG. 2, the topical intra-uterine anesthesia device includes, generally, an intrauterine applicator 24 attached to a syringe 22. The syringe 22 may be a conventional, commercially available type. The syringe 22 may be partially or wholly filled with a liquid, gel, or paste anesthetic, typically about 1–10 cc. Although the choice of anesthetic depends on the physician, a gel or paste type anesthetic is believed to be most effective for use in the uterus. One advantage of using a gel or paste type anesthetic is that it will remain in contact with the mucosa longer than a liquid anesthetic. The syringe 22 includes an injection opening 31 and includes a plunger 32 which is operated to inject the anesthetic into the desired region of the patient's body.

The applicator 20 is configured to attach to the injection opening 31 of the syringe 22 by any desired means, such as a conventional Luer Lock. The applicator 20 has a thin, hollow, slightly inclined, frontal tube 24, having an orifice at the distal tip of the tube 28 and one or more orifices 30 on the sidewalls of the frontal tube 24 near the distal tip 28. The frontal tube 24 is preferably made of a semi-flexible plastic, such as a bio-compatible silicone-based elastomer or other material appropriate for the particular application. Features may be added to make the frontal tube 24 visible under ultrasonographic or radiographic conditions. For example, a radio opaque object (such as a metallic wire) may be embedded along the length of the frontal tube 24

The frontal tube 24 may be of varying size to accommodate the needs of the patient. However, the frontal tube 24 is typically about 30 cm in length. The frontal tube 24 is typically cylindrical in shape, although the diameter of the frontal tube 24 may vary along its length. Similarly, the distal tip 28 of the frontal tube 24 may be of any shape, however, it is typically circular, having an outer diameter of about 3-4 mm. One embodiment of the frontal tube 24 involves limiting the tube's size to less than about 4 mm to permit insertion of the frontal tube 24 into the uterus without prior dilation of the cervix.

The frontal tube 24 is preferably curved at the distal end to accommodate the natural shape of the uterus and to help increase the directionality of the anesthetic flowing through the tube. The curved portion of the frontal tube 24 typically begins at about 7 cm from the distal tip 28 of the frontal tube 24 and has an angle of curvature of about 30°.

FIG. 2(b) depicts the distal end of the frontal tube 24 in greater detail. The distal end of the frontal tube 24 has several orifices. One of the orifices 26 is at the distal tip 28 of the frontal tube 24 and the remaining orifices 30 are along the sidewalls of the frontal tube 24. Although the illustrated embodiment of the frontal tube 24 has two orifices 30 in the sidewalls of the frontal tube 24, this number may vary. The side orifices 30 of the frontal tube 24 perforate the wall of the frontal tube 24 in such a way that the anesthetic exits the frontal tube 24 preferably in a forward oblique direction. This forward oblique direction of the anesthetic favors the flow of the anesthetic along the fundus and toward the uterine horn, thereby displacing any intra-uterine debris towards the corpus, through the cervix and eventually out into the vagina. The preferential flow is maintained after the frontal tube 24 has been gently advanced into the uterine cavity until the fundus is perceived.

Figure 3:
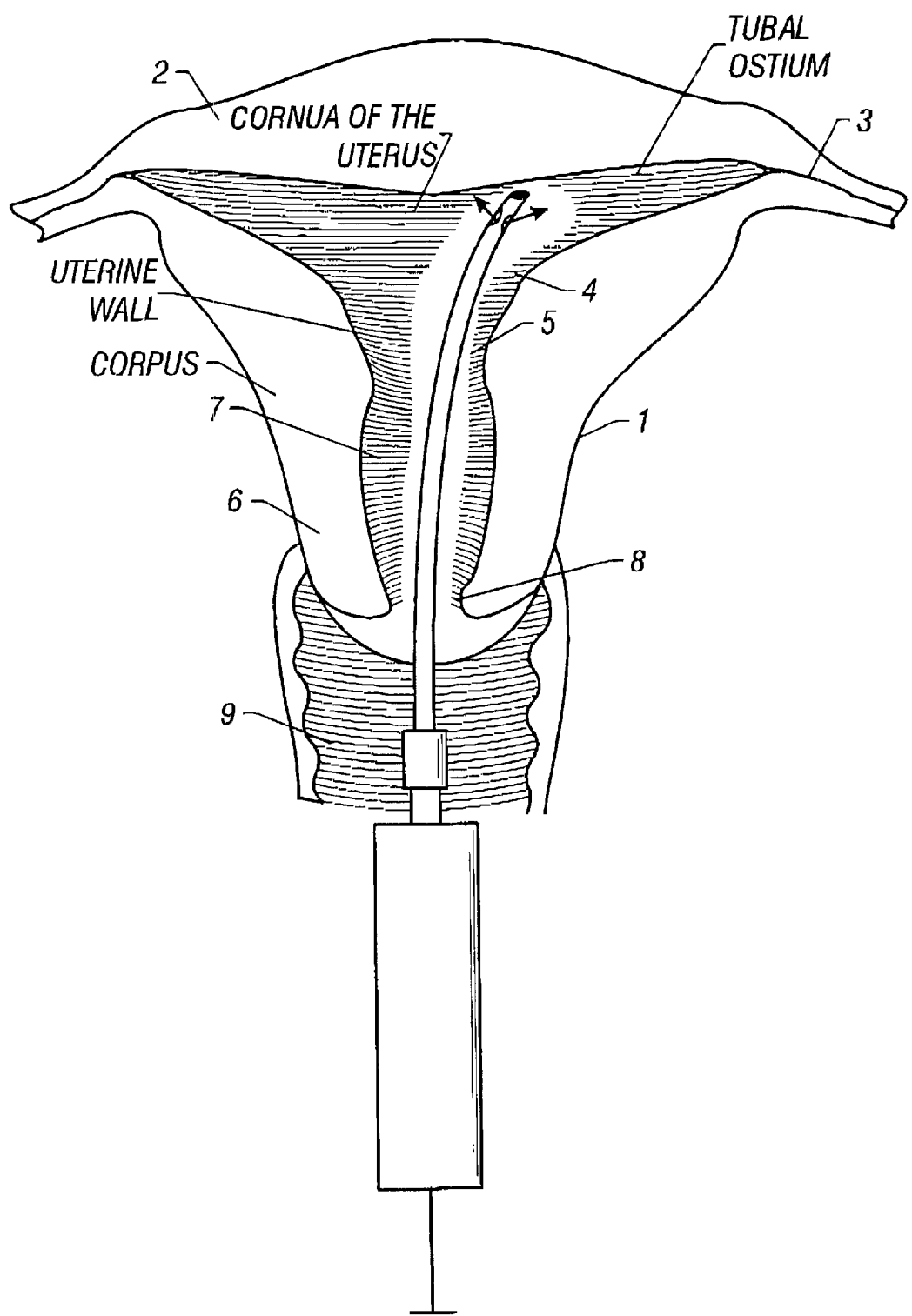
FIG. 3 is a schematic view of the topical intra-uterine anesthesia device according to one embodiment of the present invention depicting its placement in a uterus.

FIG. 3 depicts a cross-sectional view of the placement of the topical intra-uterine device in the uterus. In use, the applicator 20 is inserted through the vagina into the cervical cavity, and is gently pushed inwardly until the fundus is perceived. The plunger 32 of the syringe 22 is operated (e.g., by pushing forward) to cause the anesthetic to exit the frontal tube 24 through the orifices 30 along the sidewalls of the frontal tube 24. The orifices 30 on the side of the frontal tube 24 are further shaped to guide the anesthetic towards the tubal ostium. The anesthetic exits the distal tip of the frontal tube 24 at sufficient pressure to help guide debris present in the uterine cavity out of the uterus and towards the cervical canal for eventual exit through the vagina.

The physician may opt to hold the frontal tube 24 at the level of the middle of the fundus such that the anesthetic exits the orifices 30 towards both cornua simultaneously, provided there is no anatomical anomaly. Alternatively, the physician may opt to hold the frontal tube 24 in the direction of one or the other cornua. In this case, one or more of the side orifices 30 may be blocked and the anesthetic exits through the orifice 26 at the distal tip 28 into the direction of the tubal ostium.

After administering an effective dose of anesthetic, the applicator 20 is then withdrawn from the uterus through the vagina. If the applicator 24 is used without an acorn for preventing the back-flow of the anesthetic, observing back-flow of the anesthetic may provide evidence of the sufficiency of use of the anesthetic. The procedure of applying topical anesthesia to the mucosal surface of the uterus and uterine horn may be performed prior to or after intra-uterine manipulation/surgery. A total of approximately 10cc of anesthetic is typically sufficient for combined pre- and post surgery.

An advantage of the invention is that the anesthetic is administered into the uterus and in the direction of the tubal ostium. This ensures that the anesthetic displaces intrauterine debris away from the mucosal surface of the uterus. The anesthetic is typically more effective if it contacts the mucosal surface of the uterus directly.

In addition, further embodiments may employ different numbers of frontal tubes in the applicator as necessary for attachment to a variety of devices and/or sources necessary for different operative procedures. For example, a frontal tube may be designated for the introduction of other instruments for use in the patient's uterus. Also, it will be recognized other optical devices (e.g., a flexible fiber endoscope) may be used in conjunction with the IUAD to observe the anesthetic application procedure. For example, another embodiment of the present invention allows for video documentation of the anesthesia procedure if desired. Also, another embodiment includes a suction/irrigation port proximal to the distal tip of the frontal tube.

Another embodiment of the present invention involves using a conventional method to apply anesthetic to the cervix prior to or after the use of the present invention to apply anesthetic to the tubal ostium. Use of the conventional method to apply anesthetic to the cervix prior to or after applying the anesthetic to the tubal ostium may be used to prevent or cure discomfort resulting from the insertion of the frontal tube through the internal os of the cervix.

Another embodiment of the present invention involves the concurrent use of the IUAD with other instruments used for intrauterine manipulation/surgery. The IUAD may be incorporated into the other instrument or used alongside such instrument. Another embodiment of the present invention involves use of the IUAD for continuous application of anesthetic during an intrauterine manipulation/surgery.

The presently disclosed embodiments are to be considered in all respects as illustrative and not restrictive. The scope of the invention being indicated by the appended claims, rather than the foregoing description, and any and all changes that fall within the meaning and range of equivalency are, therefore, intended to be embraced therein.

What is claimed is:

1. A topical anesthesia device comprising:
   an injection device suitable for containing a selected amount of topical anesthetic and having an injection opening;
   means for applying topical anesthesia to the fundus of a uterus, said means comprising a hollow tube having a length sufficient to reach the fundus of the uterus through a vagina and cervix and comprising a distal end and a proximal end and sidewalls disposed between such ends, the proximal end of the tube connected to the injection opening of the injection device, the distal end of the tube having an angle of curvature and at least two orifices with at least one orifice on the sidewall of the tube adjacent to the distal tip of the tube and at least one orifice on the distal tip of the tube; and
   a junction between the injection device and the hollow tube, said junction lacking an occlusion device, thereby enabling a backflow of fluid through the vagina and cervix during application of the topical anesthetic,
   wherein the tube is adapted to be inserted through the vagina and cervix until the resistance of the fundus is perceived, and
   wherein the injection device is operable to inject anesthetic through the orifices of the tube in the region of the tubal ostium and/or the cornua of the uterus such that the anesthetic displaces intrauterine debris to reach the mucosal surface of the uterus.

2. The topical intra-uterine anesthesia device of claim 1 wherein said frontal tube is made of semi-flexible plastic.

3. The topical intra-uterine anesthesia device of claim 1 wherein said frontal tube is made of semi-flexible bio-compatible silicone based elastomer material.

4. The topical intra-uterine anesthesia device of claim 1 wherein said frontal tube is less than about 4 mm in diameter at any point so as to permit insertion of the frontal tube into the uterus without prior dilation of the cervix.

5. The topical intra-uterine anesthesia device of claim 1 wherein said frontal tube is made of a material visible to ultrasound.

6. The topical intra-uterine anesthesia device of claim 1 wherein said frontal tube is made of a radio opaque material.

7. A method for applying topical intra-uterine anesthesia using the device of claim 1, the method comprising:
   (a) inserting the applicator into the uterus through the vagina and cervix until resistance by the fundus is perceived, the fundus blocking the orifice at the distal tip of the tube; and
   (b) causing a viscous anesthetic in the injection device to exit through the orifices on the sidewalls of the tube.

8. The method of claim 7 wherein the anesthetic is a paste anesthetic.

9. The method of claim 7 wherein the anesthetic is a gel anesthetic.

10. A topical anesthesia device comprising:
    an injection device suitable for containing a selected amount of topical anesthetic and having an injection opening;
    means for applying topical intra-uterine anesthesia to the fundus of a uterus, said means comprising a hollow tube having a length sufficient to reach the fundus of the uterus when inserted through a vagina and cervix, said tube comprising a distal end and a proximal end and sidewalls disposed between such ends, the proximal end of the tube connected to the injection opening of the injection device and the distal end of the tube having an angle of curvature and at least two orifices with at least one orifice on the sidewall of the tube adjacent to the distal tip of the tube; and
    a junction between the injection device and the hollow tube, said junctions lacking an occlusion device, thereby enabling a backflow of fluid through the vagina and cervix during application of the topical anesthetic.

11. A method for applying topical anesthesia using the device of claim 11, the method comprising:
    (a) inserting the applicator into the uterus through the vagina and cervix until resistance by the fundus is perceived, the fundus blocking the orifice at the distal tip of the tube; and
    (b) causing a viscous anesthetic in the injection device to exit through the orifices on the sidewalls of the tube.

12. The topical anesthesia device of claim 10, wherein said frontal tube is made of semi-flexible plastic.

13. The topical anesthesia device of claim 10, wherein said frontal tube is made of semi-flexible bio-compatible silicone based elastomer material.

14. The topical anesthesia device of claim 10, wherein said frontal tube is made of a material visible to ultrasound.

15. The topical anesthesia device of claim 10, wherein said frontal tube is made of a radio opaque material.

16. The topical anesthesia device of claim 10, wherein said frontal tube is less than about 4 mm in diameter at any point so as to permit insertion of the frontal tube into the uterus without prior dilation of the cervix.

* * * * *